United States Patent [19]

Inoue et al.

[11] Patent Number: 4,773,424
[45] Date of Patent: Sep. 27, 1988

[54] ELECTROCARDIOGRAPHIC ELECTRODE

[75] Inventors: Hirokatsu Inoue, Chiba; Chuji Shimizu, Funabashi, both of Japan

[73] Assignee: Fukuda Denshi Co., Ltd., Tokyo, Japan

[21] Appl. No.: 910,717

[22] Filed: Sep. 24, 1986

[30] Foreign Application Priority Data

Oct. 2, 1985 [JP] Japan .............................. 60-151378[U]

[51] Int. Cl.$^4$ ............................................. A61B 5/04
[52] U.S. Cl. .................................................. 128/641
[58] Field of Search ............................. 128/639–641, 128/644, 798, 802, 803

[56] References Cited

U.S. PATENT DOCUMENTS

| | | | |
|---|---|---|---|
| 3,834,373 | 9/1974 | Sato ........................................ | 128/640 |
| 3,911,906 | 10/1975 | Reinhold, Jr. ......................... | 128/641 |
| 4,082,086 | 4/1978 | Page et al. .............................. | 128/640 |
| 4,488,557 | 12/1984 | Engel ...................................... | 128/641 X |

Primary Examiner—Lee S. Cohen
Attorney, Agent, or Firm—Pollock, VandeSande & Priddy

[57] ABSTRACT

An electrocardiographic electrode is disclosed, which is to be held in close contact with a person's skin for deriving a weak voltage from an inner part of the person. The electrode includes a viscous base member to be held in close contact with the person's skin and having a central opening, a reinforcement member bonded to the front surface of the viscous base member to close the opening, a lead connector hook penetrating a central portion of the reinforcement member to be coupled to a lead connector, and an electrode member secured to the underside of the lead connector hook. The viscous base member with the central opening is viscous both on the back surface to be held in close contact with the skin and on the front surface coupled to the lead connector.

5 Claims, 3 Drawing Sheets

PRIOR ART

PRIOR ART

ELECTROCARDIOGRAPHIC ELECTRODE

BACKGROUND OF THE INVENTION

1. Field of the Invention

This invention relates to an electrocardiographic electrode for deriving a weak voltage from a person and, more particularly, to an electrocardiographic electrode having a structure, in which a water-proof suction member for covering the electrocardiographic electrode held in close contact with a person's skin is strongly bonded to the electrocardiographic electrode so that it will not be detached therefrom.

2. Prior Art

As is well known in the art, electricity generated in a person is induced by the activity of the heart, brain, muscles, etc.

Particularly, electricity induced in the heart is derived and recorded as a weak voltage induced on the person's skin using an external electrocardiograph. When the electrocardiograph is used, its input section is electrically coupled to the person. To this end, electrocardiographic electrodes have to be held in close contact with the person's skin.

A prior art electrocardiographic electrode which is held in close contact with man's skin in use will now be described with reference to FIGS. 4 to 6. FIG. 4 is a perspective view of electrocardiographic electrode 1. The electrocardiographic electrode has a substantially circular, viscous base member 2. The viscous base member 2 is a doughnut-like woven cloth member having a central aperture or opening 3. Its back side, which is held in close contact with the person's skin M as shown in FIG. 6, is viscous. The opening 3 of the viscous base member 2 is closed by an electrode support 4, which consists of a hard synthetic resin and is formed on the top or front side of the viscous base member 2. A magnetic lead coupler 5 projects from the front surface of the electrode support 4. An electrode member 6 is secured to the lower or back surface of the lead coupler 5. The electrode member 6 is held in direct contact with the person's skin M to derive a weak voltage from the person's heart.

FIG. 5 shows the back side of the lead coupler or connector 7. A lead 10 is coupled to the lead coupler 7 for leading the heart's weak voltage derived by the electrode member 6 through the lead 10 to the electrocardiograph (not shown). The lead connector 7 has substantially the same size as the electrocardiographic electrode and is made of a hard resin. It has a recess 8 formed on the back side. A magnetic electrode coupler 9 is accommodated in the recess 8 and secured to the bottom thereof. One end of the lead 10 is connected to the electrode coupler 9, and its other end is connected to the electrocardiograph (not shown).

To obtain an electrocardiogram using the electrocardiographic electrode 1 having the above construction, the viscous base member 2 of the electrode 1 is bonded to a person's skin M, as shown in FIG. 6. Then, the lead connector 7 is coupled to the electrocardiographic electrode 1 with its magnetic electrode coupler 9 magnetically attracted to the lead coupler 5 of the electrocardiographic electrode 1. In this state, a heart's weak voltage derived by the electrode member 6 is coupled through the lead 10 to the electrocardiograph (not shown) for recording.

While the electrocardiographic electrode 1 is held in close contact with the patient's skin for obtaining a patient's electrocardiogram, it is liable that the lead connector 7 coupled to the electrode 1 is detached from the electrode due to an unconscious movement, e.g., a tossing-about in sleep. In such a case, noise is produced so that an accurate electrocardiogram can no longer be obtained.

Further, the patient sometimes unconsciously pulls out the lead 10 extending from the lead connector 7. If the lead 10 is pulled extremely strongly, again detachment of the lead connector 7 from the electrocardiographic electrode 1 results, so that an accurate electrocardiogram can no longer be obtained.

Further, the patient may take a bath with electrocardiographic electrodes held in close contact with the skin. Also, an electrocardiogram is sometimes produced while the patient is making a physical exercise, e.g., swimming. In such cases, a water-proof suction member is used to cover the electrocardiographic electrode together with the lead connector. However, it is liable that the water-proof suction member is detached by the action of water so that an accurate electrocardiogram can no longer be obtained.

SUMMARY OF THE INVENTION

An object of the invention is to provide an electrocardiographic electrode which can solve the above problems and permit an accurate electrocardiogram to be reliably obtained.

According to the invention, there is provided an electrocardiographic electrode to be held in close contact with a person's skin for deriving a weak voltage from an inner part of the person comprising a viscous base member to be held in close contact with the person's skin and having a central opening, a reinforcement member bonded to the front surface of the viscous base member to close the opening, a lead connector hook penetrating a central portion of the reinforcement member to be coupled to a lead connector, and an electrode member secured to the underside of the lead connector hook, the viscous base member with the central opening being viscous both on the back side to be held in close contact with the skin and on the front side coupled to the lead connector.

DETAILED DESCRIPTION OF THE PREFERRED EMBODIMENT

Figure 1:
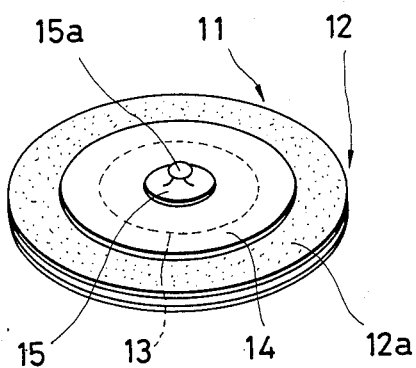
FIG. 1 is a perspective view showing the front side of an embodiment of the electrocardiographic electrode according to the invention.
Figure 2:
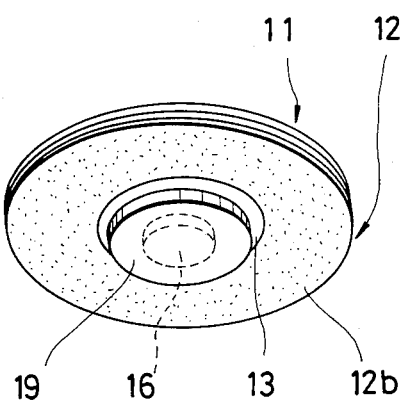
FIG. 2 is a perspective view showing the back side of the electrocardiographic electrode.

An embodiment of the invention will now be described in conjunction with its constitution and operation with reference to the drawings. FIG. 1 is a perspective view showing the front side of an embodiment of the electrocardiographic electrode according to the invention, and FIG. 2 is a perspective view showing the back side of the electrocardiographic electrode of FIG. 1. The electrocardiographic electrode is designated at 11.

The electrocardiographic electrode 11 has a viscous base member 12. The viscous member 12 is a doughnut-like member having a central aperture or opening 13. The detailed structure of the viscous base member 12 will be described later.

The central opening 13 of the viscous base member 12 is closed by a disk-like reinforcement member 14 which is bonded to the top or front surface of the viscous base member 12. As shown in FIG. 1, the reinforcement member 14 has a smaller diameter than the viscous base member 12 and is made of vinyl chloride.

Figure 3:
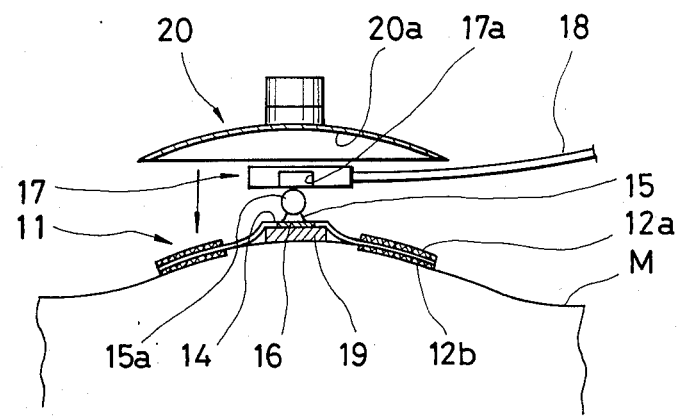
FIG. 3 is a view for explaining the use of the electrocardiographic electrode.
Figure 4:
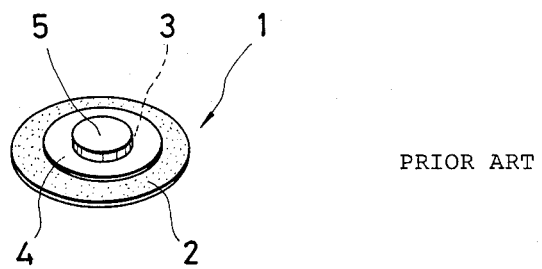
FIGS. 4 and 6 are views for explaining a prior art electrocardiographic electrode.
Figure 5:
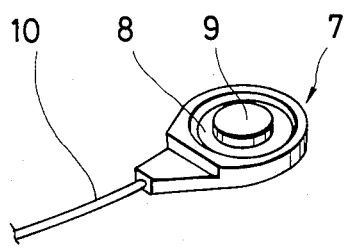
Figure 6:
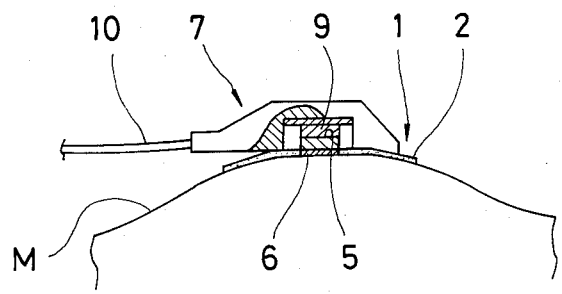

A lead connector hook 15 is made of a metal and penetrates the center of the reinforcement member 14. The lead connector hook 15 has a lead coupler 15a projecting from its top. A flat electrode member 16 made of Ag-AgCl is connected to the bottom of the lead connector hook 15, as shown in FIG. 2. A lead connector 17 with a lead 18, as shown in FIG. 3, is coupled to the projecting lead coupler 15a The other end of the lead 18 is connected to an electrocardiograph (not shown).

An electrode member cover 19, as shown in FIG. 2, is bonded to the electrode member 16. The cover 19 consists of a water-containing gel layer prepared from glutine, agar, polyacrylamide, etc. It has considerable viscosity and also has electric conductivity.

The electrode member cover 19 is held in close contact with the skin to lead a weak voltage induced on the skin to the electrode member 16. Without the electrode member cover 19, i.e., if the electrode member 16 is held in direct base contact with the skin, the weak voltage cannot be accurately measured due to the contact resistance offered by the skin surface. Heretofore, it has been in practice to apply beforehand cream or the like to the skin to reduce the contact resistance, and the electrode member 16 is held in contact with the cream for the measurement of the weak voltage. To apply cream whenever the measurement of the weak voltage is done, however, is cumbersome and inefficient. The water-containing gel layer noted above, bonded to the electrode member 16, serves the role of the cream and eliminates the inconvenience of applying cream for each time of measurement. The water-containing gel layer as the electrode member cover 19 may be replaced with a polyurethane foam layer impregnated with jelly.

The viscous base member 12, as shown in FIGS. 1 and 2, is disk-like and obtained using foamed polyurethane, an independently foamed butadiene rubber sheet non-woven cloth and a woven cloth. The viscous base member 12 manufactured using the independently foamed butadiene sheet has excellent cushioning property and light soft touch, so that the electrocardiographic electrode can be conveniently held in close contact with the person's skin.

As shown in FIG. 2, the back surface 12b of the viscous base member 12 is made viscous in order to obtain close contact of the electrocardiographic electrode 11 with the person's skin M as shown in FIG. 3. Further, the viscous base member 12 is viscous not only on the back surface 12b but also on the front surface 12a, as shown in FIG. 1, so that a water-proof suction member 20 as shown in FIG. 3 can be bonded to it.

The lead connector 17 is made of a metal, and it has an engagement hole 17a formed substantially in its central portion. The lead coupler 15a of the lead connector hook 15 of the electrocardiographic electrode 11 is coupled to the engagement hole 17a.

The electrocardiographic electrode 11 having the above construction is used as follows. First, the back surface 12b of the viscous base member 12 of the electrocardiographic electrode 11 is held in close contact with person's skin M, as shown in FIG. 3. Then, the lead connector 17 is coupled to the electrocardiographic electrode 11 by fitting its engagement hole 17a on the lead coupler 15a of the lead connector hook 15 of the electrocardiographic electrode 11 in close contact with the person's skin M. Thereafter, the water-proof suction member 20 is fitted to cover the lead connector 17 and electrocardiographic electrode 11 coupled together. At this time, the inner surface 20a of the water-proof suction member 20 is held in close contact with the front surface 12a of the viscous base member 12. Since the front surface 12a of the viscous base member 12 is viscous, the inner surface 20a of the water-proof suction member 20 is bonded to the surface 12a. Thus, the water-proof suction member 20 is firmly bonded to and never detached from the electrocardiographic electrode 11.

As has been described in the foregoing, according to the invention the viscous base member is made viscous on both the front and back sides, so that the water-proof suction member can be held firmly bonded to and never detached from the electrocardiographic electrode. It is thus possible to obtain an electrocardiograph of a patient while the patient is taking a bath or exercises.

Further, the effect of preventing the detachment of the water-proof suction member from the electrocardiographic electrode can be obtained very simply and inexpensively by merely making both the front and back surfaces of the viscous base member viscous.

What is claimed is:

1. An electrocardiographic electrode to be held in close contact with a person's skin for deriving a weak voltage from an inner part of the person, comprising:
    a viscous base member to be held in close contact with the person's skin, said viscous base member having front and back viscous surfaces and a central opening;
    a reinforcement member bonded to the front surface of said viscous base member to close said opening;
    a lead connector hook penetrating a central portion of said reinforcement member, said connector hook having a portion coupled to a lead connector;
    an electrode member coupled to said connector hook for relaying the weak voltage from the person's skin; and
    a waterproof suction electrode member securely covering the portion of said lead connector hook and said front surface of said viscous member;
    wherein, insofar as said viscous base member with said central opening is viscous both on the front and back surfaces, the back surface of said base member is held in intimate contact with the skin; and
    said front surface of said base member is firmly bonded to said waterproof suction electrode member.

2. The electrocardiographic electrode according to claim 1, wherein both of said front and back surfaces of said viscous base member are made of a viscous foamed resin.

3. The electrocardiographic electrode according to claim 1, wherein both of said front and back surfaces of said viscous base member are made from rubber sheets formed independently on said front and back surfaces.

4. The electrocardiographic electrode according to claim 1, wherein both of said front and back surfaces of said viscous base member are made of non-woven cloths.

5. The electrocardiographic electrode according to claim 1, wherein both of said front and back surfaces of said viscous base member are made of viscous woven cloths.

* * * * *

UNITED STATES PATENT AND TRADEMARK OFFICE
CERTIFICATE OF CORRECTION

PATENT NO. : 4,773,424
DATED : September 27, 1988
INVENTOR(S) : Hirokatsu Inoue, et al.

It is certified that error appears in the above-identified patent and that said Letters Patent is hereby corrected as shown below:

Column 1, line 26, change "man's" to --the person's--.

Column 4, line 5, after "with" insert --the--.

Signed and Sealed this

Twenty-eighth Day of February, 1989

*Attest:*

DONALD J. QUIGG

*Attesting Officer*     *Commissioner of Patents and Trademarks*